United States Patent [19]
Fushimi et al.

[11] Patent Number: 6,118,019
[45] Date of Patent: Sep. 12, 2000

[54] 3-ALKOXYPROPIONIC ESTER DERIVATIVE

[75] Inventors: Masaki Fushimi; Shintaro Inazawa, both of Oita, Japan

[73] Assignee: Showa Denko K.K., Tokyo, Japan

[21] Appl. No.: 09/221,849

[22] Filed: Dec. 29, 1998

Related U.S. Application Data

[62] Division of application No. 08/535,514, Sep. 28, 1995.

[30] Foreign Application Priority Data

Sep. 28, 1994 [JP] Japan .................................. 6-259143
Nov. 18, 1994 [JP] Japan .................................. 6-285249
Nov. 28, 1994 [JP] Japan .................................. 6-293226

[51] Int. Cl.$^7$ .................................................... C07C 69/74
[52] U.S. Cl. ........................... 560/116; 560/55; 560/56; 560/60; 560/61; 560/118; 560/119; 560/121; 560/122; 560/123; 560/124; 560/126; 560/128; 560/183; 560/187; 560/188
[58] Field of Search .................................. 560/187, 116, 560/118, 121, 122, 123, 124, 126, 128, 183, 188, 56, 119, 60, 61

[56] References Cited

U.S. PATENT DOCUMENTS

| | | | |
|---|---|---|---|
| 4,187,196 | 2/1980 | Giannini et al. ................. | 252/429 B |
| 4,785,133 | 11/1988 | Raynolds et al. ................. | 560/187 |
| 4,827,021 | 5/1989 | Jones et al. ....................... | 560/187 |
| 5,041,403 | 8/1991 | Nakajo et al. ..................... | 502/104 |

FOREIGN PATENT DOCUMENTS 0 383 346 A2  8/1990  European Pat. Off. .

OTHER PUBLICATIONS

Villieras, Preparation . . . Reactive, Journal of Organometallic Chemistry, vol. 102, No. 2, pp. 129–140, Dec. 1975.

*Primary Examiner*—Rosalynd Keys
*Attorney, Agent, or Firm*—Sughrue, Mion, Zinn, Macpeak & Seas, PLLC

[57] ABSTRACT

A 3-alkoxypropionic ester derivative, an olefin polymerization solid catalyst component using the same, an olefin polymerization catalyst using the same, and a process for the preparation of a polyolefin using the same. The 3-alkoxypropionic ester derivative is represented by formula (I):

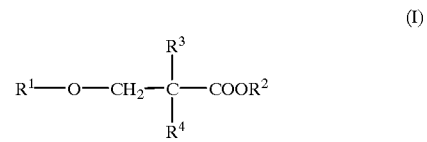

wherein $R^1$ represents a hydrocarbon group having from 1 to 10 carbon atoms; $R^2$ represents a hydrocarbon group having from 1 to 20 carbon atoms; $R^3$ represents a hydrocarbon group having from 1 to 20 carbon atoms; and $R^4$ represents a branched hydrocarbon group having 3 or more carbon atoms.

5 Claims, 5 Drawing Sheets

3-ALKOXYPROPIONIC ESTER DERIVATIVE

This is a divisional of application Ser. No. 08/535,514, filed Sep. 28, 1995, the disclosure of which is incorporated herein by reference.

FIELD OF THE INVENTION

The present invention relates to a novel 3-alkoxypropionic ester derivative useful as an electron donor for Ziegler-Natta catalyst for the preparation of polyolefins. The present invention relates to a catalyst for the preparation of a polyolefin using the foregoing 3-alkoxypropionic ester derivative and a process for the preparation of a polyolefin in the presence of such a catalyst.

BACKGROUND OF THE INVENTION

A Ziegler-Natta catalyst for the preparation of a polyolefin mainly composed of an organoaluminum compound and a transition metal compound of Groups III to V has heretofore been used with a compound having an electron donative group to enhance the activity thereof. The reason for the enhancement of the activity is unknown at present. The recent studies suggest that the electron donor to be used needs to satisfy the following requirements:

(1) The compound contains an ester group and an alkoxy group in its molecule; and (2) The compound contains a bulky substituent which gives steric hindrance in its molecule.

The inventors previously confirmed on the basis of the foregoing presumption that the use of a 3-alkoxy-2-alkyl-substituted ester propionate represented by the general formula:

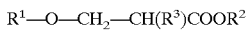

$$R^1\text{—O—}CH_2\text{—}CH(R^3)COOR^2$$

wherein $R^1$, $R^2$ and $R^3$ each represent an alkyl group, can provide improved catalyst properties, as disclosed in JP-A-2-289604 (The term "JP-A" as used herein means an "unexamined published Japanese patent application").

However, many electron donors which have heretofore been proposed, including the foregoing electron donors, cannot necessarily satisfy high industrial requirements for catalyst properties such as high activity, high stereoregularity and high productivity any more.

The inventors presumed that one of the most effective solutions for improving the properties of a Ziegler-Natta catalyst is to use a compound having an ester group and an alkoxy group in its molecule and two bulky alkyl groups on the carbon atom at the α-position with respect to the ester group as an electron donor. None of these compounds have been reported in any references probably due to the steric hindrance of the bulky alkyl group at the α-position with respect to the ester group or probably because their application was not expected at all.

The inventors sought for a novel compound containing an ester group and an alkoxy group in its molecule and two alkyl groups, particularly bulky alkyl substituents on the carbon atom in a position alpha to the ester group on the basis of the foregoing presumption.

Heretofore, many solid catalyst components made of a magnesium compound, a titanium compound, a halogen compound and an electron donor as essential components have been proposed as catalyst components.

It is well known that these catalysts exhibit a high activity in the polymerization of olefin. It is also well known that these catalysts exhibit a high stereospecificity in the polymerization of α-olefin.

It is further known that such a solid catalyst component prepared from an alkyl phthalate compound as an electron donor can exhibit excellent properties on polymerization.

In a catalyst system comprising this ester phthalate compound as an electron donor, it is necessary that a large amount of an organosilicon compound be used as a co-catalyst component in addition to organoaluminum compound. However, the organosilicon compound to be used for the foregoing purpose has a bulky structure and thus is expensive. Thus, it causes a problem in the catalyst cost. Further, siloxanes or inorganic silicate produced by the decomposition of the foregoing organosilicon compound are microdispersed and left in the polymer and thus have a great affect on the physical properties of the polymer.

The inventors previously found that the use of an organic compound having a specific structure as an electron donor for catalyst can provide a solid catalyst component which can exhibit some stereoregularity without using an organosilicon compound as a co-catalyst component (as disclosed in EP38334A). However, practicable properties cannot be obtained only by the use of the solid catalyst and organoaluminum compound. Thus, in the actual use, such a solid catalyst component must comprise an organosilicon compound, though in a small amount, incorporated therein.

In recent years, studies have been made on the use of diether compounds as electron donors (as disclosed in JP-A-3-294302). However, diether compounds have a high potential that they have a physiological activity from the structural standpoint of view. Therefore, diether compounds must be carefully handled. Thus, diether compounds have problems in safety.

It is well known that an electron donor is used as a co-catalyst component of a magnesium chloride-supported Ziegler-Natta catalyst. Many reports have been made that alkyl benzoates, piperidines, acetals or organosilicon compounds (alkoxysilane) are useful as electron donors. However, among these compounds, alkyl benzoates or piperidines have an inherent odor. When these compounds are used as electron donors, an odor remaining in the product can often cause troubles. Further, acetal compounds are liable to deactivation of the catalyst, resulting in the increase of catalyst cost.

Accordingly, an organosilicon compound (alkoxysilane) is normally often used for the foregoing purpose. It is well known that an organosilicon compound, particularly alkoxysilane compound, can easily undergo hydrolysis due to water content in the air or the like, giving the corresponding silanol compound or siloxane compound. Therefore, if an organosilicon compound is used as an electron donor for catalyst, the resulting polymer often contains a silanol compound or siloxane compound.

Heretofore, such a catalyst residue, etc. has been removed by deliming process. In recent years, however, more olefin polymerization plants have employed a non-deliming process or non-pelletizing process more often. Therefore, it has happened more often that product polymers having catalyst residues left therein are on the market.

However, the silanol compound or siloxane compound microdispersed in the polymer can often cause the drop in the physical properties, particularly rigidity, of the polymer. Thus, all of the inherent physical properties of the polymer cannot be necessarily exerted.

It has been keenly desired to develop a catalyst system which is free of organosilicon compound as a co-catalyst component and causes no safety problems, and a catalyst system which exhibits excellent properties without using any organosilicon compound which is a source of a silanol compound or siloxane compound as an electron donative component for olefin polymerization catalyst.

SUMMARY OF THE INVENTION

It is therefore an object of the present invention to provide a novel 3-alkoxypropionic ester derivative as a compound having an ester group and an alkoxy group in its molecule, the ester group having two bulky substituents on the carbon atom at the a-position with respect to the ester group, and a process for the preparation thereof. This 3-alkoxypropionic ester derivative is a compound useful as an electron donor for Ziegler-Natta catalyst which exhibits a high activity and a high stereoregularity.

It is another object of the present invention to provide an olefin polymerization solid catalyst component which is free of any expensive organosilicon compound as a cocatalyst component, causes no safety problems and exhibits a high activity and a high stereoregularity, an olefin polymerization catalyst using the same and a process for the preparation of an olefin polymer using the same.

It is a further object of the present invention to provide an olefin polymerization catalyst which exhibits a high activity and a high stereoregularity in the preparation of a polyolefin in the presence of a supported Ziegler catalyst and is free of a silanol compound which causes a drop of physical properties, especially rigidity, of the resulting polymer or an organosilicon compound which becomes as a source of siloxanes and a process for the preparation of an olefin polymer in the presence of such an olefin polymerization catalyst.

These and other objects of the present invention will become more apparent from the following detailed description and examples.

The present invention relates to, as a first embodiment, a 3-alkoxypropionic ester derivative, represented by formula (I):

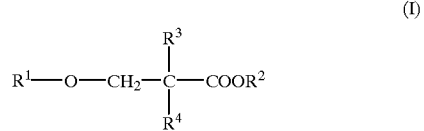

wherein $R^1$ represents a hydrocarbon group having from 1 to 10 carbon atoms; $R^2$ represents a hydrocarbon group having from 1 to 20 carbon atoms; $R^3$ represents a hydrocarbon group having from 1 to 20 carbon atoms; and $R^4$ represents a branched hydrocarbon group having 3 or more carbon atoms.

The 3-alkoxypropionic ester derivative according to the present invention wherein $R^1$ is a methyl group, $R^2$ is a lower alkyl group having from 1 to 4 carbon atoms, $R^3$ is an isopropyl group, and $R^4$ is an isopentyl group, i.e., a 3-methoxy-2-isopropyl-2-isopentylpropionic alkyl ester represented by formula (Ia), is preferred:

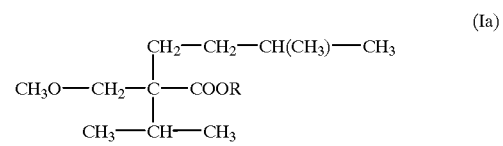

wherein R is a lower alkyl group having from 1 to 4 carbon atoms.

The 3-alkoxypropionic ester derivative of the first embodiment represented by formula (I) will be hereinafter occasionally referred to as an "electron donor" in connection with a polymerization solid catalyst component and a polymerization catalyst.

The present invention also relates to, as a second embodiment, an olefin polymerization solid catalyst component comprising a magnesium compound, a titanium compound, a halogen compound, and the foregoing electron donor of the first embodiment.

The present invention further relates to, as a third embodiment, an olefin polymerization catalyst comprising (a) the olefin polymerization solid catalyst component of the second embodiment and (b) an organoaluminum compound.

The present invention further relates to, as a fourth embodiment, an olefin polymerization catalyst comprising (A) a solid catalyst component comprising a titanium compound, a magnesium compound, and a halogen compound, (B) an organoaluminum compound, and (C) the electron donor of the first embodiment.

The present invention further relates to, as a fifth embodiment, a process for the preparation of an olefin polymer, which comprises the step of polymerizing an olefin in the presence of an olefin polymerization catalyst in the presence of the olefin polymerization catalyst of the third or fourth embodiment.

The present invention further relates to, as a sixth embodiment, a process for the preparation of a 3-methoxy-2-isopropyl-2-isopentylpropionic alkyl ester represented by formula (Ia), which comprises the step of reacting a 3-hydroxy-2-isopropyl-2-isopentylpropionic alkyl ester with a halogenated methyl or methyl paratoluenesulfonate in the presence of a dehalogenating agent, or the step of reacting a 3-methoxy-2-isopropyl-2-isopentylpropionic compound with an alcohol.

The present invention further provides a novel 2-formyl-2-isopropyl-5-methyl-hexanoic alkyl ester represented by formula (II) and a novel 3-hydroxy-2-isopropyl-2-isopentylpropionic alkyl ester represented by formula (III), as intermediates of the 3-methoxy-2-isopropyl-2-isopentylpropionic alkyl ester represented by formula (Ia):

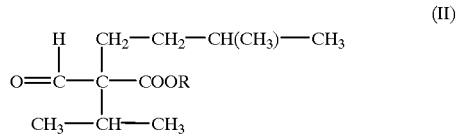

wherein R represents a lower alkyl group having from 1 to 4 carbon atoms,

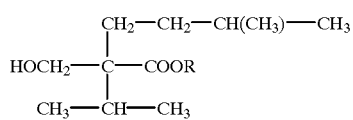

(III)

wherein R represents a lower alkyl group having from 1 to 4 carbon atoms.

BRIEF DESCRIPTION OF THE DRAWINGS

By way of example and to make the description more clear, reference is made to the accompanying drawings in which.

DETAILED DESCRIPTION OF THE INVENTION

Figure 1:
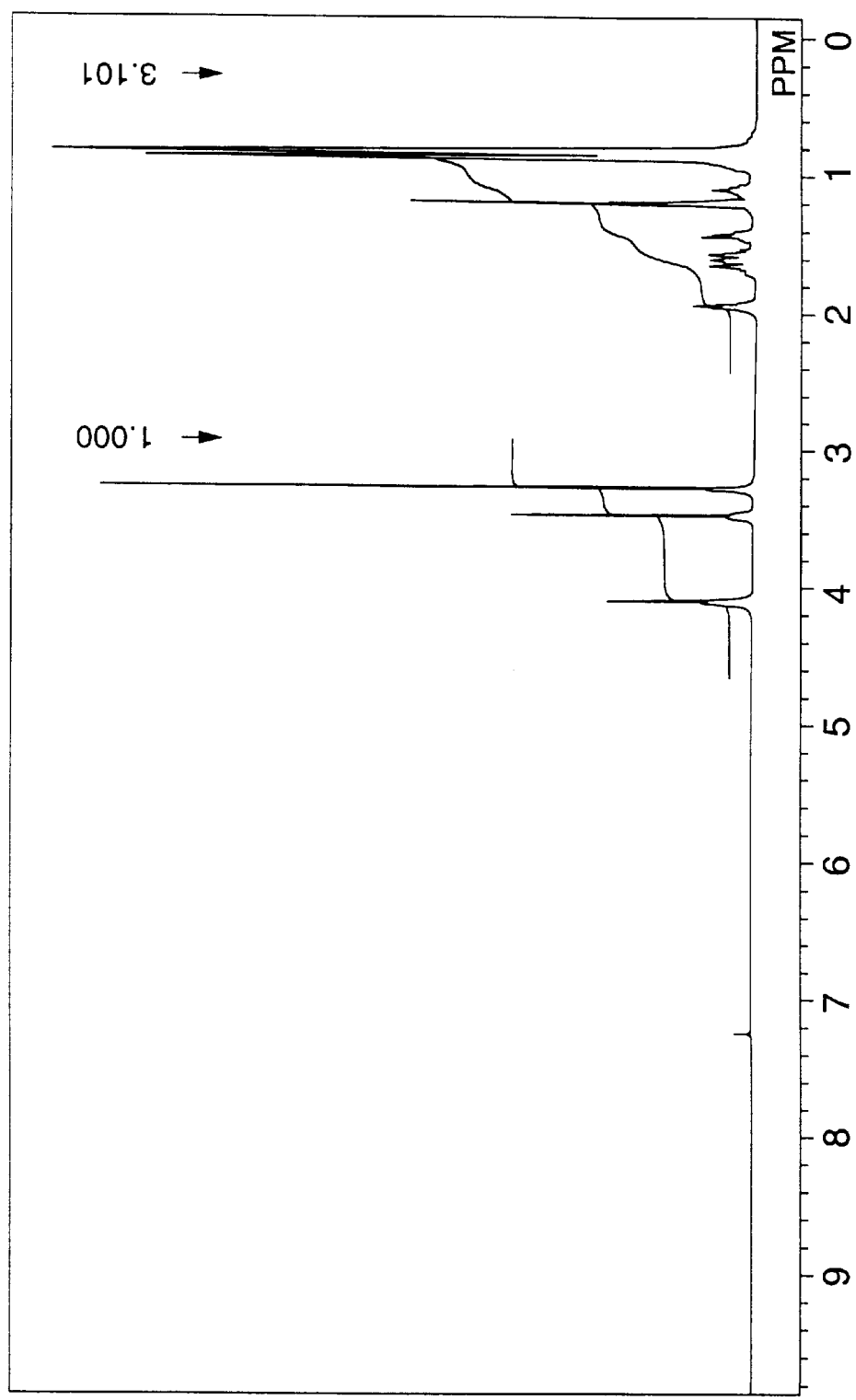
FIG. 1 is $^1$H-NMR chart of ethyl 3-methoxy-2-isopropyl-2-isopentylpropionate produced in Example 1.

The first embodiment of the present invention will be further described with reference to 3-methoxy-2-isopropyl-2-isopentylpropionic ethyl ester by way of example, but the present invention should not be construed as being limited thereto.

The foregoing ethyl ester can be obtained in the form of crude product, e.g., by the reaction of 3-hydroxy-2-isopropyl-2-isopentylpropionic ethyl with a methyl halogenide $CH_3X$ (in which X is chlorine, bromine, iodine, paratoluenesulfonic acid or the like) in a solvent in the presence of a dehydrohalogenating agent. Preferred examples of the solvent include a protonic solvent such as alcohol, polar solvent such as ether or the like. Examples of the dehydrohalogenating agent to be present in the reaction including sodium, potassium, sodium hydride, potassium hydride or the like. Preferred examples of $CH_3X$ include methyl iodide, methyl bromide or methyl chloride. In general, the preparation process may comprise the addition of a methyl halogenide to the reaction system, followed by the reaction at a temperature of from 20° C. to 200° C. for 1 to 24 hours.

3-Hydroxy-2-isopropyl-2-isopentylpropionic ethyl to be used as a starting material in the foregoing reaction can be synthesized by the reduction reaction of the corresponding aldehyde compound. For example, ethyl 2-formyl-2-isopropyl-5-methyl-hexanoate may be reacted with an organometal compound in a solvent to obtain the desired compound. Preferred examples of the solvent include an alcohol or the like. As the organometal compound, a compound having a weak reducing power is normally preferred, and sodium boron hydride or the like is useful. In general, the reaction may be effected at a temperature of from −78° C. to 200° C. for 1 to 24 hours.

The foregoing ethyl 2-formyl-2-isopropyl-5-methyl-hexanoate can be produced by Cannizzaro reaction of 2-isopropyl-2-isopentyl-ethyl acetate with an alkaline formaldehyde.

The ethyl 2-formyl-2-isopropyl-5-methyl-hexanoate can be synthesized also by the selective partial reduction reaction of the corresponding diester compound. Specifically, diethyl 2-isopropyl-2-isopentylmalonate may be reacted with an organometal compound in a solvent to prepare the desired compound. Examples of the solvent include a polar solvent such as ether, hydrocarbon solvent such as hexane or aromatic hydrocarbon solvent such as toluene. Examples of the organometal compound include sodium aluminum hydride, lithium aluminum alkoxide, diisobutyl aluminum hydride, hydrosilane, hydrotin or the like. Preferred among these organometal compounds is diisobutyl aluminum hydride. The temperature at which the organometal compound is brought into contact with diethyl 2-isopropyl-2-isopentylmalonate is from −100° C. to 50° C., preferably from −78° C. to 0° C. The reaction time depends on the kind of the organometal compound used and is generally from 1 to 24 hours.

It has heretofore been extremely difficult to produce a 2-formyl-2-isopropyl-5-methyl-hexanoic alkyl ester depending on the general synthesis method by the partial reduction of a diester compound represented by formula (IV):

(IV)

In other words, when the alkyl groups represented by $R^5$ and $R^6$ are small (e.g., when both $R^5$ and $R^6$ are isobutyl groups), it is extremely difficult to partially reduce the diester compound to produce a 2,2-dialkyl-substituted 2-formyl-acetic ester.

However, in the combination of $R^5$ and $R^6$ that are an isopropyl group and an isopentyl group, respectively, one of the dicarboxylic acid ester groups can be selectively reduced to the corresponding aldehyde.

The ethyl 2-formyl-2-isopropyl-5-methyl-hexanoate can be synthesized also by the esterification reaction of 3-methoxy-2-isopropyl-2-isopentylpropionic acid or its acid chloride rather than by the methoxylation of the hydroxyl group at the 3-position. For example, ethyl 2-formyl-2-isopropyl-5-methyl-hexanoate in the form of crude product was obtained by esterification of 3-methoxy-2-isopropyl-2-isopentylpropionic acid with ethanol in the presence of a catalyst.

The crude product thus obtained can then be subjected to purification by distillation to obtain the desired compound.

Ethyl 3-methoxy-2-isopropyl-2-isopentylpropionate thus purified is a colorless liquid having a boiling point of from 126.5 to 127° C./13 mmHg. This product can be confirmed by $^1$H-NMR, $^{13}$C-NMR, GC-MS, etc.

For example, when this product was analyzed by $^1$H-NMR, the following characteristic peaks were observed:

(1) Peak of hydrogen atom connected to carbon atom directly connected to oxygen atom in ethyl group in ester group was confirmed at δ=4.096 ppm;

(2) Peak of hydrogen atom positioned in the 3-position of propane skeleton was confirmed at δ=3.472 ppm;

(3) Peak of hydrogen atom connected to carbon atom in methoxy group was confirmed at δ=3.273 ppm;

(4) Peak of hydrogen atom connected to carbon atom on methyl group in isopropyl group was confirmed at δ=1.948 ppm;

(5) Peak of hydrogen atom connected to carbon atom on methylene group in isopentyl group was confirmed at δ=1.663 to 1.570 ppm;

(6) Peak of hydrogen atom connected to carbon atom on methine group in isopentyl group was confirmed at δ=1.446 ppm;

(7) Peak of hydrogen atom connected to methyl carbon atom in ethyl group was confirmed at δ=1.214 ppm;

(8) Peak of hydrogen atom connected to carbon atom on methylene group in isopentyl group was confirmed at δ=1.149 to 1.087 ppm;

(9) Peak of hydrogen atom connected to carbon atom on methylene group in isopentyl group was confirmed at δ=0.962 to 0.927 ppm;

(10) Peak of hydrogen atom connected to carbon atom on methyl group in isopropyl group was confirmed at δ=0.898 ppm; and

(11) Peak of hydrogen atom connected to carbon atom in methyl group in isopentyl group was confirmed at δ=0.842 ppm.

Further, when this product was analyzed by $^{13}$C-NMR, peaks were observed at 174.91 ppm, 72.34 ppm, 59.88 ppm, 52.96 ppm, 33.59 ppm, 32.22 ppm, 29.44 ppm, 28.62 ppm, 22.57 ppm, (18.24, 18.08) and 14.28 ppm. Thus, this compound was confirmed to be a mixture of D-racemate and L-racemate.

The electron donor of the first embodiment of the present invention represented by formula (I) is useful as an electron donor for Ziegler-Natta catalyst for the preparation of a polyolefin. The electron donor of the present invention can be used as an "internal donor" which is produced by processing the solid catalyst component constituting the Ziegler-Natta catalyst with the electron donor or can be used as an "external donor" which is used with the solid catalyst component and the organoaluminum compound in combination.

The olefin polymerization solid catalyst component of the second embodiment of the present invention comprising a magnesium compound, a titanium compound, a halogen compound and an electron donor (internal donor) of the present invention, the olefin polymerization catalyst of the third embodiment of the present invention comprising the foregoing solid catalyst component and organoaluminum compound, and a process for the preparation of a polyolefin in the presence of the foregoing catalyst will be described hereinafter.

Figure 4:
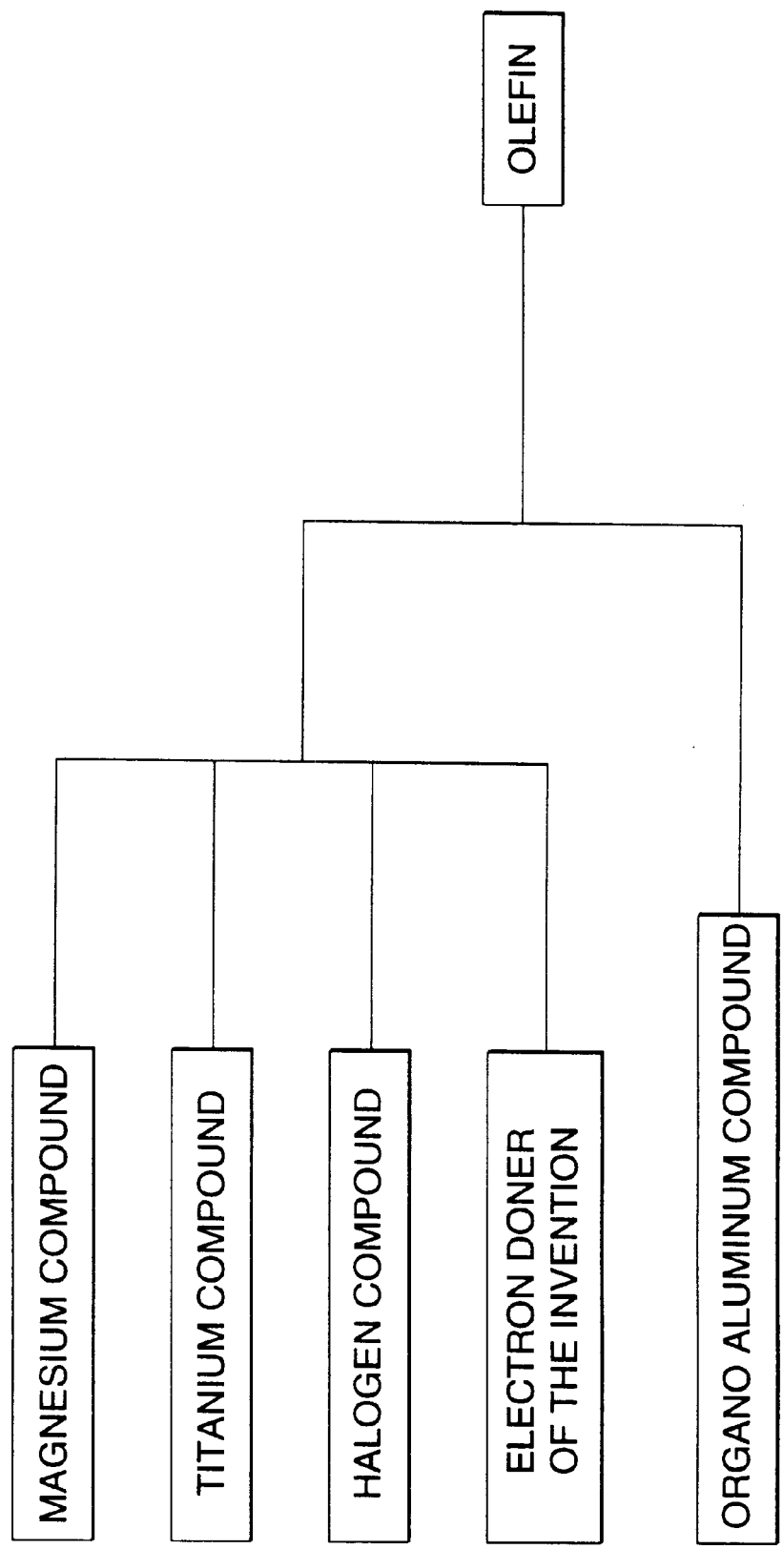
FIG. 4 is a flow chart of the preparation method wherein an electron donor of the present invention is used as an internal donor.

FIG. 4 is a flow chart of the process for the preparation of a polyolefin wherein an electron donor of the present invention is used as an internal donor.

Examples of the magnesium compound employable herein include magnesium halogenide such as magnesium chloride and magnesium bromide, alkoxy magnesium such as ethoxy magnesium and isopropoxy magnesium, carboxylate of magnesium such as magnesium laurate and magnesium stearate, and alkyl magnesium such as butyl ethyl magnesium. Two or more of these magnesium compounds may be used in admixture. In a preferred embodiment, a magnesium halogenide may be used. In another preferred embodiment, a magnesium compound may be used such that a magnesium halogenide is produced during the formation of the catalyst. In a further preferred embodiment, the halogen in the preferred embodiments is chlorine.

Examples of the titanium compound employable herein include titanium halogenide such as titanium tetrachloride, titanium trichloride and titanium tetrabromide, titanium alkoxide such as titanium butoxide and titanium ethoxide, and alkoxy titanium halide such as phenoxy titanium chloride. Two or more of these compounds may be used in admixture. The titanium compound to be used herein is preferably a tetravalent titanium compound containing halogen, particularly titanium tetrachloride.

In the halogen-containing compound to be used in the present invention, the halogen is generally fluorine, chlorine, bromine or iodine, and preferably chlorine. Specific compounds which can be exemplified depend on the process for the preparation of the catalyst. Representative examples of the halogen-containing compound employable herein include titanium halogenide such as titanium tetrabromide, silicon halogenide such as silicon tetrachloride and silicon tetrabromide, phosphorus halogenide such as phosphorus trichloride and phosphorus pentachloride, and halogen-containing alcohol such as 2,2,2-trichloroethanol and 2,2,2-trifluoroethanol. Depending on the process for the preparation of the catalyst, halogenated hydrocarbon, halogen molecule and halogenated hydro-acid (e.g., HCl, HBr, HI) may also be used.

The electron donor to be used in the present invention is a compound represented by formula (I):

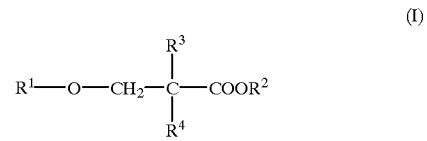

In formula (I), $R^1$ is a $C_{1-10}$ hydrocarbon group, preferably $C_{1-5}$ hydrocarbon group, more preferably $C_{1-15}$ hydrocarbon group, such as a methyl group, an ethyl group and a propyl group. (The expressions "$C_{1-10}$" and the like used herein mean "having from 1 to 10 carbon atoms" and the like.)

$R^2$ is a $C_{1-20}$ hydrocarbon group, preferably $C_{1-15}$ hydrocarbon group, more preferably a $C_{1-10}$ hydrocarbon group, such as a methyl group, an ethyl group, a propyl group, an isopropyl group, a butyl group, an isobutyl group, a pentyl group, an isopentyl group, a hexyl group, a heptyl group, an octyl group, a 2-ethylhexyl group, a cyclopentyl group and a cyclohexyl group.

$R^3$ is a $C_{1-20}$ hydrocarbon group, preferably a $C_{1-15}$ hydrocarbon group, such as a methyl group, an ethyl group, a propyl group, an isopropyl group, a butyl group, an isobutyl group, a pentyl group, an isopentyl group, a hexyl group, a heptyl group, an octyl group, a 2-ethylhexyl group, a decyl group, a pentadecyl group, a cyclopentyl group and a cyclohexyl group.

$R^4$ is a hydrocarbon group having 3 or more carbon atoms, preferably a branched hydrocarbon group having 3 or more carbon atoms, such as an isopropyl group, an isobutyl group, a sec-butyl group, a tert-butyl group, an isopentyl group, a sec-pentyl group, a tert-pentyl group, a 2-ethylhexyl group, a dexyl group, a cyclopentyl group or a cyclohexyl group.

Examples of the foregoing compound include methyl 2-methyl-2-isopropyl-3-methoxy-propionate, ethyl 2-methyl-2-isopropyl-3-propionate, iso-butyl 2-methyl-2-isopropyl-3-methoxy-propionate, tert-butyl 2-methyl-2-isopropyl-3-methoxy-propionate, 2-ethylhexyl 2-methyl-2-isopropyl-3-methoxy-propionate, methyl 2-methyl-2-isopropyl-3-ethoxy-propionate, ethyl 2-methyl-2-isopropyl-3-ethoxy-propionate, butyl 2-methyl-2-isopropyl-3-ethoxy-propionate, ethyl 2-ethyl-2-isopropyl-3-methoxy-propionate, butyl 2-ethyl-2-isopropyl-isopropyl-3-methoxy-propionate, tert-butyl 2-ethyl-2-isopropyl-3-methoxy-propionate, 2-ethylhexyl 2-ethyl-2-isopropyl-3-methoxypropionate, ethyl 2,2-diisopropyl-3-methoxy-propionate, butyl 2,2-diisopropyl-3-methoxy-propionate, methyl 2-isopropyl-2-isobutyl-3-methoxy-propionate, ethyl 2-isopropyl-2-isobutyl-3-methoxy-propionate, butyl 2-isopropyl-2-isobutyl-3-methoxy-propionate, 2-ethylhexyl 2-isopropyl-2-isobutyl-3-methoxy-propionate, methyl 2-isopropyl-2-isopentyl-3-methoxy-propionate, ethyl 2-isopropyl-2-isopentyl-3-methoxy-propionate, butyl 2-isopropyl-2-isopentyl-3-methoxy-propionate, 2-ethylhexyl 2-isopropyl-2-isopentyl -3-methoxy-propionate, methyl 2-isopropyl-2-cyclopentyl-3-methoxy-propionate, ethyl 2-isopropyl-2-cyclopentyl-3-methoxy-propionate, butyl 2-isopropyl-2-cyclopentyl-3-methoxy-propionate, 2-ethylhexyl 2-isopropyl-2-cyclopentyl -3-methoxy-propionate, butyl 2-isopropyl- 2-cyclohexyl-3-methoxy-propionate, 2-ethylhexyl 2-isopropyl-2-cyclohexyl-3-methoxy-propionate, 2-ethylhexyl 2-butyl-2-isopropyl-3-methoxy-propionate, ethyl 2-butyl-2-isobutyl-3-methoxy-propionate, 2-ethylhexyl 2-butyl-2-isobutyl-3-methoxy-propionate, ethyl 2-butyl-2-isopentyl-3-methoxy-propionate, 2-ethylhexyl 2-butyl-2-isopentyl-3-methoxy-propionate, ethyl 2-butyl-2-cyclopentyl-3-methoxy-propionate, ethyl 2,2-diisobutyl-3-methoxy-propionate, 2-ethylhexyl 2,2-diisobutyl-3-methoxy-propionate, ethyl 2-isobutyl-2-isopentyl-3-methoxy-propionate, 2-ethylhexyl 2-isobutyl-2-isopentyl-3-methoxy-propionate, ethyl 2-isobutyl-2-cyclopentyl-3-methoxy-propionate, 2-ethylhexyl 2-isobutyl-2-cyclopentyl-3-methoxy-propionate, methyl 2-cyclopentyl-2-isopentyl-3-methoxy-propionate, ethyl 2-cyclopentyl-2-isopentyl-3-methoxy-propionate, butyl 2-cyclopentyl-2-isopentyl-3-methoxy-propionate, 2-ethylhexyl 2-cyclopentyl-2-isopentyl-3-methoxy-propionate, and ethyl 2,2-dicyclopentyl-3-methoxy-propionate.

Among the above compounds, ethyl 2,2-diisobutyl-3-methoxy-propionate, methyl 2-isopropyl-2isopentyl-3-methoxy-propionate, ethyl 2-isopropyl-2-isopentyl-3-methoxy-propionate, methyl 2-isopropyl-2-cyclopentyl-3-methoxy-propionate, ethyl 2-isopropyl-2-cyclopentyl-3-methoxy-propionate, methyl 2-cyclopentyl-2-isopentyl-3-methoxy-propionate, ethyl 2-cyclopentyl-2-isopentyl-3-methoxy-propionate, methyl 2,2-dicyclopentyl-3-methoxy-propionate, and ethyl 2,2-dicyclopentyl-3-methoxy-propionate are preferably used.

The process for the preparation of the catalyst to be used herein is not specifically limited. In general, a magnesium halogenide, a titanium halogenide and an electron donor of the present invention may be ground together, and then halogenated to obtain a higher activity. Alternatively, a magnesium halogenide may be ground, singly or in combination with a silicon compound or phosphorus compound, and then subjected to treatment with a titanium compound or halogenation in the presence of an electron donor. Further, a magnesium carboxylate or alkoxy magnesium may be subjected to heat treatment with a titanium compound, a halogenating agent and an electron donor to obtain a higher activity. Further, a solution of a magnesium halogenide in an organic solvent may be treated with an electron donor of the present invention during or after the precipitation in the presence of a titanium compound. Further, the catalyst may be prepared by adding an electron donor and a titanium compound when an alkyl magnesium is treated with a halogenating agent.

The remaining amount of the electron donor in the catalyst depends on the preparation method. The molar ratio of titanium/magnesium/E.D. (electron donor) is generally 1/1 to 1000/10$^{-6}$ to 100, preferably 1/1 to 1000/10$^{-4}$ to 10.

If the molar proportion of E.D. falls below this range, the resulting stereoregularity tends to be reduced. If the molar proportion exceeds this range, the resulting activity tends to be reduced.

The olefin polymerization catalyst of the third embodiment of the present invention will be described in detail below.

As the solid catalyst component of the polymerization catalyst of the third embodiment, the solid catalyst component according to the second embodiment of the present invention can be used.

Typical examples of the organoaluminum compound to be used in the third embodiment of the present invention include compounds represented by formulae (V), (VI), and (VII):

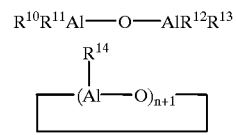

and/or

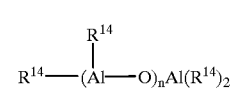

In formulae (V), (VI), and (VII), $R^7$, $R^8$ and $R^9$ may be the same or different and each represent a hydrocarbon group having 12 or less carbon atoms, a halogen atom or a hydrogen atom, provided that at least one of $R^7$, $R^8$ and $R^9$ is a hydrocarbon group; $R^{10}$, $R^{11}$, $R^{12}$ and $R^{13}$ may be the same or different and each represent a hydrocarbon group having 12 or less carbon atoms; $R^{14}$ represents a hydrocarbon group having 12 or less carbon atoms; and n represents an integer of not less than 1.

Representative examples of the organoaluminum compound represented by formula (V) include a trialkyl aluminum such as triethyl aluminum, tripropyl aluminum, tributyl aluminum, triisobutyl aluminum, trihexyl aluminum and trioctyl aluminum; an alkyl aluminum hydride such as diethyl aluminum hydride and diisobutyl aluminum hydride; and an alkyl aluminum halide such as diethyl aluminum chloride, diethyl aluminum bromide and ethyl aluminum sesquichloride.

Representative examples of the organoaluminum compound represented by formula (VI) include an alkyl dialumoxane such as tetraethyl dialumoxane and tetrabutyl alumoxane.

The compound represented by formula (VII) is an aluminoxane, which is a polymer of an aluminum compound. $R^{14}$ represents a methyl group, an ethyl group, a propyl group, a butyl group, a pentyl group or the like, preferably a methyl group or an ethyl group; and n preferably represents an integer of from 1 to 10.

Preferred among these organoaluminum compounds are a trialkyl aluminum, an alkyl aluminum halide, and an alkyl alumoxane. Particularly preferred among these organoaluminum compounds is a trialkyl aluminum, which provides excellent results.

The olefin to be polymerized is generally an olefin having 18 or less carbon atoms. Representative examples of such an olefin include ethylene, propylene, butene- 4-methylpentene-1, hexene-1, and octene-1. These olefins may be homopolymerized. Alternatively, two or more of these olefins may be copolymerized (e.g., ethylene and propylene may be copolymerized).

In the polymerization of olefin, the amount of the organoaluminum compound to be used in the polymerization system is generally not less than $10^{-4}$ mmol/l, preferably not less than $10^{-2}$ mmol/l. The molar proportion of the organoaluminum compound to titanium atom in the solid catalyst component is generally not less than 0.5, preferably not less than 2, particularly not less than 10. If the amount of the organoaluminum compound to be used is too small, the polymerization activity may be drastically reduced. When the amount of the organoaluminum compound to be used in the polymerization system is not less than 20 mmol/l and the molar proportion of the organoaluminum compound to titanium atom is not less than 1,000, the performance of the catalyst cannot be further enhanced even if these values are increased.

When the foregoing titanium-containing solid catalyst component to be used for the purpose of enhancing the stereoregularity of α-olefin polymer is used, even in a small amount, its purpose can be accomplished. However, the titanium-containing solid catalyst component is generally used in an amount of from 0.01 to 5 mol, preferably from 0.01 to 1 mol, per mol of the organoaluminum compound.

In the olefin polymerization process according to the present invention, an olefin is preferably preliminarily polymerized to the olefin polymerization catalyst.

The olefin to be preliminarily polymerized to the olefin polymerization catalyst may be the same as or different from the olefin to be used in the main polymerization process described later. Propylene is preferably used as such an olefin.

The reaction temperature in the preliminary polymerization process is from −20° C. to 100° C., preferably from −20° C. to 60° C.

In the preliminary polymerization process, a molecular weight adjustor such as hydrogen may be used.

The preliminary polymerization is preferably effected in such a manner that a polymer is produced in an amount of from 0.1 to 1,000 g, preferably from 0.3 to 500 g, particularly from 1 to 200 g, per g of the olefin polymerization catalyst.

In the polymerization process, the solid catalyst component of the present invention and the organoaluminum compound may be separately introduced into the polymerization vessel or may be previously mixed.

The polymerization may be effected in an inert solvent, a liquid monomer (olefin) or gas phase. In order to obtain a polymer having a practicable melt flow, a molecular weight adjustor (generally hydrogen) may be present in the polymerization system.

The polymerization temperature is generally from −10° C. to 180° C., practically from 20° C. to 130° C.

In the polymerization process according to the fifth embodiment of the present invention using the catalyst of the third embodiment of the present invention, other electron donor than that contained in the solid catalyst component may be used in combination as an external donor. As such an external electron donor, any of electron donors commonly used in this field of art.

As to the form of the polymerization reaction vessel, the process for controlling polymerization, the post-treatment process, etc., there are no restrictions inherent to the present catalyst system. Any known methods can be applied.

The olefin polymerization catalyst of the fourth embodiment of the present invention comprising (A) a solid catalyst component made of a titanium compound, a magnesium compound and a halogen compound, (B) an organoaluminum compound and (C) an electron donor (external donor) of the present invention and the process for the preparation of a polyolefin in the presence of the catalyst will be described hereinafter.

Figure 5:
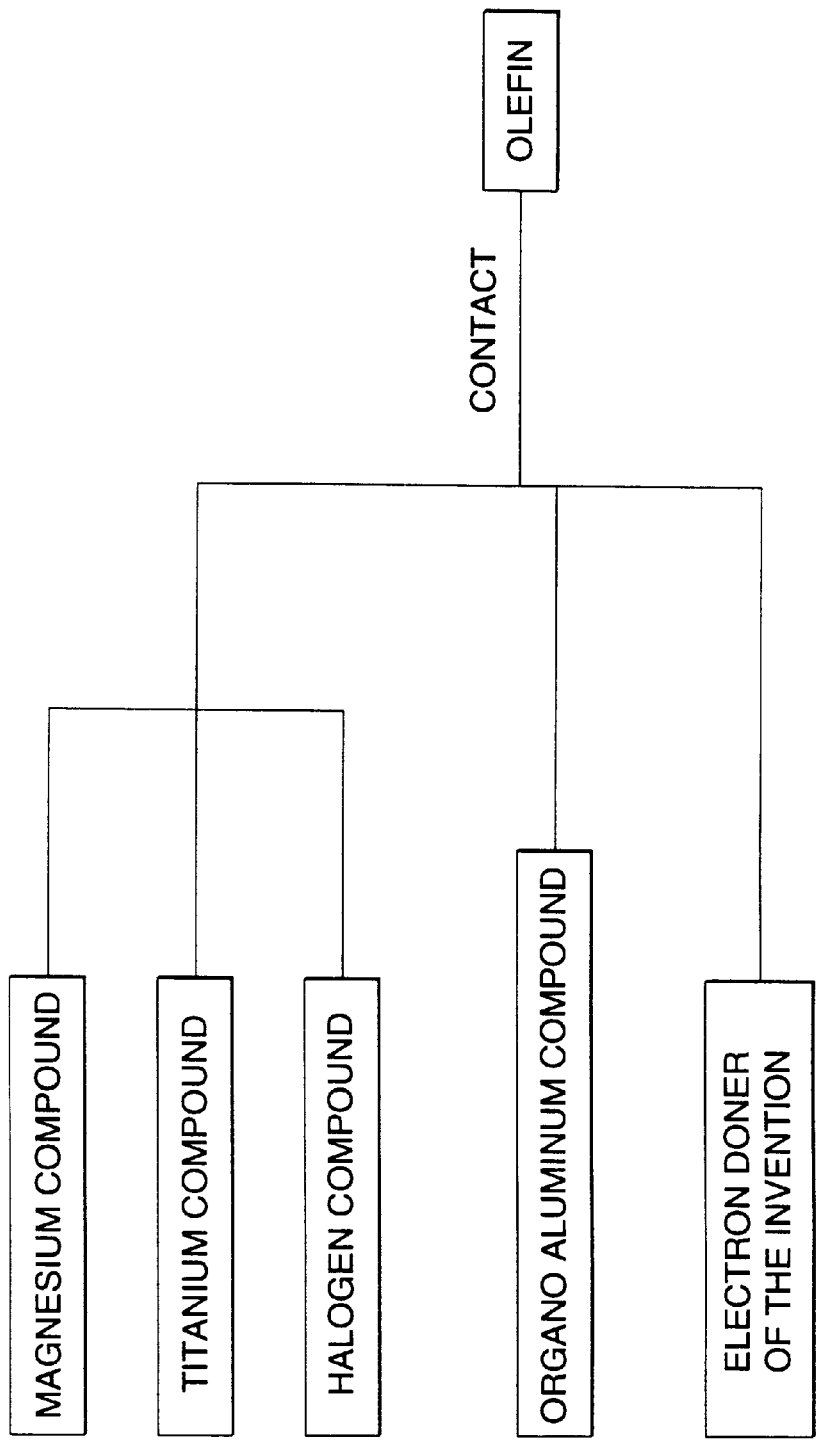
FIG. 5 is a flow chart of the preparation method wherein an electron donor of the present invention is used as an external donor.

FIG. 5 is a flow chart of the process for the preparation of a polyolefin wherein an electron donor of the present invention is used as an external donor.

As the magnesium compound, the titanium compound, and the halogen compound to be used in the fourth embodiment of the present invention, those exemplified with reference to the second embodiment of the present invention can also be employed.

In the preparation of the solid catalyst component (A) to be used in the fourth embodiment of the present invention, various electron donors (internal donors) may be preferably added to the reaction system. Examples of the electron donors include oxygen-containing compounds and nitrogen-containing compounds. Specific examples of these electron donors include:

(i) $C_{1-20}$ alcohols such as methanol, ethanol, propanol, butanol, heptanol, hexanol, octanol, dodecanol, octadecyl alchol, 2-ethylhexyl alcohol, benzyl alcohol, cumyl alcohol, diphenyl methanol and triphenyl methanol, (ii) $C_{6-25}$ phenols which may contain alkyl group, such as phenol, cresol, ethyl phenol, propyl phenol, cumyl phenol, nonyl phenol and naphthol, (iii) $C_{3-15}$ ketones such as acetone, methyl ethyl ketone, methyl isobutyl ketone, acetophenone and cyclohexanone, (iv) $C_{2-15}$ aldehydes such as acetaldehyde, propionaldehyde, tolualdehyde and naphthoaldehyde, (v) $C_{2-20}$ organic esters such as methyl formate, ethyl formate, methyl acetate, ethyl acetate, propyl acetate, octyl acetate, cyclohexyl acetate, methyl cellosolve acetate, cellosolve acetate, ethyl propionate, n-methyl acetate, methyl isobutyrate, ethyl isobutyrate, isopropyl isobutyrate, ethyl valerate, butyl valerate, ethyl stearate, methyl chloroacetate, ethyl dichloroacetate, methyl methacrylate, ethyl methacrylate, ethyl crotonate, ethyl cyclohexanecarboxylate, methyl phenylacetate, methyl phenylacetate, propyl phenylacetate, methyl benzoate, ethyl benzoate, propyl benzoate, butyl benzoate, octyl benzoate, cyclohexyl benzoate, phenyl benzoate, benzyl benzoate, cellosolve benzoate, methyl toluylate, ethyl toluylate, amyl toluylate, ethylbenzoate, methyl anisate, ethyl ethoxybenzoate, diethyl phthalate, diisobutyl phthalate, diheptyl phthalate, dineopentyl phthalate, γ-butyrolactone, γ-valerolactone, cumarin, phthalide, diethyl carbonate, methyl orthoformate and ethyl orthoformate, (vi) alkoxy esters such as methyl methoxyacetate, ethyl methoxyacetate, butyl methoxyacetate, phenyl methoxyacetate, methyl ethoxyacetate, ethyl ethoxyacetate, butyl ethoxyacetate, phenyl ethoxyacetate, ethyl n-propoxyacetate, ethyl i-propoxyacetate, methyl n-butoxyacetate, ethyl i-butoxyacetate, ethyl n-hexyloxyacetate, octyl sec-hexyloxyacetate, methyl 2-methylcyclohexyloxyacetate, methyl 3-methoxypropionate, ethyl 3-methoxypropionate, butyl 3-methoxypropionate, ethyl 3-ethoxypropionate, butyl 3-ethoxypropionate, n-octyl 3-ethoxypropionate, dodecyl 3-ethoxypropionate, pentamethylphenyl 3-ethoxypropionate, ethyl 3-(i-propoxy)propionate, butyl 3-(i-propoxy)propionate, allyl 3-(n-propoxy)propionate, cyclohexyl 3-(n-butoxy)propionate, ethyl 3-neopentyloxypropionate, butyl 3-(n-octyloxy)propionate, octyl 3-(2,6-dimethyldecyloxy)propionate, ethyl 4-ethoxyacetate, cyclohexyl 4-ethoxyacetate, octyl 5-(n-propoxy)valerate, ethyl 12-ethoxylaurate, ethyl 3-(1-indenoxy)propionate, methyl 2-ethoxyacrylate, ethyl 3-phenoxyacrylate, ethyl 2-methoxypropionate, n-butyl 2-(i-propoxy)acetate, methyl 2-ethoxyisoacetate, phenyl 2-cyclohexyloxyisovalerate, butyl 2-ethoxy-2-phenylacetate, allyl 3-neopentyloxybutyrate, methyl 3-ethoxy-3-(o-methylphenyl)propionate, ethyl 3-ethoxy-2-(o-methylphenyl)propionate, ethyl 4-ethoxy-2-methyl-1-naphthylnonanoate, ethylester 2-methoxycyclopentanecarboxylate, butylester 2-ethoxycyclohexanecarboxylate, isopropylester 3-(ethoxymethyl)tetralin-2-acetate, ethylester 8-butoxy-decalin-1-carboxylate, methylester 3-ethoxynorbornane-2-carboxylate, methyl 2-(phenoxy)acetate, ethyl 3-(p-cresoxy)propionate, methyl 4-(2-naphthoxy)acetate, butyl 5-carbaloxyvalerate, methyl 2-phenoxypropionate, ethyl 3-(4-methylphenoxy)-2-phenylpropionate, ethylester 2-phenoxycyclohexanecarboxylate, ethyl thiophene-3-oxyacetate, ethyl 2-(2-picolinoxymethyl)-cyclohexanecarboxylate, ethyl 3-furfuryloxypropionate, ethyl 2,2-diisobutyl-3-methoxy-propionate, methyl 2-isopropyl-2-isopentyl-3-propionate, ethyl 2-isopropyl-2-isopentyl-3-methoxy-propionate, methyl 2-isopropyl-2-cyclopentyl-3-methoxy-propionate, ethyl 2-isopropyl-2-cyclopentyl-3-methoxy-propionate, methyl 2-cyclopentyl-2-isopentyl-3-methoxy-propionate, ethyl 2-cyclopentyl-2-isopentyl-3-methoxy-propionate, methyl 2,2-dicyclopentyl-3-methoxy-propionate and ethyl 2,2-dicyclopentyl-3-methoxy-propionate, (vii) ketoesters such as methyl acetylacetate, ethyl acetylacetate, butyl acetylacetate, methyl propionylacetate, phenyl acetylacetate, ethyl propionylacetate, ethyl propionylacetate, phenylpropionylacetate, butyl propionylacetate, ethyl butyrylacetate, ethyl i-butanoylacetate, ethyl pentanoylacetate, methyl 3-acetylpropionate, ethyl 3-acetylpropionate, butyl 3-acetylpropionate, ethyl 3-propionylpropionate, butyl 3-propionylpropionate, n-octyl 3-propionylpropionate, dodecyl 3-propionylpropionate, pentamethylphenyl 3-propionylpropionate, ethyl 3-(i-propionyl)propionate, butyl 3-(i-propionyl)propionate, allyl 3-(i-propionyl)propionate, cyclohexyl 3-(i-propionyl)propionate, ethyl 3-neopentanoylpropionate, butyl 3-n-laurylpropionate, methyl 3-(2,6-dimethylhexanoyl)propionate, ethyl 4-propionylbutyrate, cyclohexyl 4-propionylacetate, octyl 5-butyrylvalerate, ethyl 12-butyryllaurate, methyl 3-acetylacrylate, methyl 2-acetylacrylate, ethyl 3-benzoylpropionate, methyl 3-benzoylpropionate, ethyl 3-methylbenzoylpropionate, butyl 3-toluilbutyrate, ethyl o-benzoylbenzoate, ethyl m-benzoylbenzoate, ethyl p-benzoylbenzoate, butyl o-toluilbenzoate, ethyl o-toluilbenzoate, ethyl m-toluilbenzoate, ethyl p-toluilbenzoate, ethyl o-(2,4,6-trimethylbenzoyl)benzoate, ethyl m-(2,4,6-trimethylbenzoyl)benzoate, ethyl p-(2,4,6-trimethylbenzoyl) benzoate, ethyl o-ethylbenzoylbenzoate, ethyl o-acetylbenzoate, ethyl o-propionylbenzoate, ethyl o-laurylbenzoate, ethyl o-cyclohexanoylbenzoate and ethyl o-dodecylbenzoate, (viii) inorganic acid esters such as methyl borate, butyl titanate, butyl phosphate, diethyl phosphite and di(2-phenylphenyl)phosphocholidate, (ix) $C_{2-25}$ ethers such as methyl ether, ethyl ether, isopropyl ether, butyl ether, amyl ether, tetrahydrofuran, anisol, diphenyl ether, ethylene glycol diethyl ether, ethylene glycol diphenyl ether and 2,2-dimethoxypropane, (x) $C_{2-20}$ acid amides such as amide acetate, amide benzoate and amide toluylate, (xi) $C_{2-20}$ acid halides such as acetyl chloride, benzoyl chloride, toluic chloride, anisic chloride, phthaloyl chloride and isophthaloyl chloride, (xii) $C_{2-20}$ acid anhydrides such as acetic anhydride and phthalic anhydride, (xiii) $C_{1-20}$ amines such as monomethylamine, monoethylamine, diethylamine, tributylamine, piperidine, tribenzylamine, aniline, pyridine, picoline and tetramethylethylenediamine, (xiv) $C_{2-20}$ nitriles such as acetonitrile, benzonitrile and trinitrile, (xv) $C_{2-20}$ thiols such as ethyl thioalcohol, butyl thioalcohol and phenyl thiol, (xvi) $C_{4-25}$ thioethers such as diethyl thioether and diphenyl thioether, (xvii) $C_{2-20}$ sulfuric esters such as dimethyl sulfate and ethyl sulfate, (xviii) $C_{2-20}$ sulfonic acids such as phenyl methyl sulfone and diphenyl sulfone, and (xix) $C_{2-24}$ silicon-containing compounds such as phenyltrimethoxysilane, phenyltriethoxysilane, phenyltributoxysilane, vinyltriethoxysilane, diphenyldiethoxysilane, phenyldimethylmethoxysilane, phenyldimethylethoxysilane, triphenylmethoxysilane, hexamethyldisiloxane, octamethyltrisiloxane, trimethylsilanol, phenyldimethylsilanol, triphenylsilanol, diphenylsilanediol and lower alkyl of silicate (particularly ethyl silicate).

Two or more of these electron donors may be used in combination. Preferred among these electron donors are organic acid esters, alkoxyesters and ketoesters.

The process for producing a polyolefin according to the fifth embodiment of the present invention using the catalyst of the fourth embodiment of the present invention will be described below in detail.

In the polymerization process using the catalyst of the fourth embodiment, the preparation process of the catalyst, the remaining amount of the electron donor in the catalyst may be the same as those described for the second embodiment of the present invention.

The electon donor (C) used in the polymerization process is an electon donor represented by formula (I) that is used in the second embodiment of the present invention.

The amount of the electron donor (C) to be used is generally from 0.001 to 5, preferably from 0.01 to 1, as calculated in terms of molar ratio (C)/(B).

In the polymerization process, the solid catalyst component of the present invention, an organoaluminum compound, and the electron donor may be separately introduced into the polymerization vessel. Alternatively, two or all of these components may be previously mixed. Typically, an inert solvent, an organoaluminum compound and an organosilicon compound described later may be mixed in a dropping funnel the air in which has been replaced by nitrogen. After the lapse of a predetermined period of time (over about 1 minute), this mixture is preferably brought into contact with the solid catalyst component so that it is further reacted for a predetermined period of time (over about 1 minute), and then introduced into the polymerization reaction vessel. Examples of the inert solvent employable herein include alkane or cycloalkane such as pentane, hexane, heptane, n-octane, isooctane, cyclohexane and methyl cyclohexane, alkylaromatic hydrocarbon such as toluene, xylene, ethylbenzene, isopropylbenzene, ethyltoluene, n-propylbenzene, diethylbenzene, monoalkyl naphthalene and dialkyl naphthalene, halogenated or hydrogenated aromatic hydrocarbon such as chlorobenzene, chloronaphthalene, orthodichlorobenzene, tetrahydronaphthalene and decahydronaphthalene, high molecular liquid paraffin, and mixture thereof.

In the polymerization process using the catalyst of the fourth embodiment, the organoaluminum compound, the olefin to be polymerized, the polymerization process, the preliminary polymerization and the like may be the same as those used in the polymerization process using the catalyst of the third embodiment of the present invention.

The present invention will be further described in the following examples, but the present invention should not be construed as being limited thereto.

EXAMPLE 1

Synthesis of ethyl 3-methoxy-2-isopropyl-2-isopentylpropionic (1) Synthesis of ethyl 2-isopentylmalonate Into a 2-l flask equipped with an agitator, a Dimroth condenser and a dropping funnel were charged 300 ml of dried ethanol and 200 ml of sodium ethoxide (Aldrich) in a stream of nitrogen. To the mixture was then added 128 g (0.8 mol) of diethyl malonate. The reaction mixture was then stirred at room temperature for 30 minutes. To the reaction mixture were then added 92 g (0.61 mol) of isopentyl bromide and 50 ml of ethanol. The reaction mixture was then heated under reflux condition while the reaction was being followed gas chromatography. After the completion of the reaction, the reaction mixture was then poured into 500 ml of dilute hydrochloric acid. The reaction mixture was then extracted with 200 ml of pentane three times. The resulting organic phase was neutralized with a saturated sodium hydrogencarbonate, washed with a saturated ammonium chloride solution and water, and then dried over sodium sulfate. The solvent was then distilled off by means of a rotary evaporator. The residue was then distilled under reduced pressure to obtain the desired compound.

Boiling point: 127–133° C./11 mmHg
Yield: 116 g (63%)
GC>98.5%
$^1$H-NMR (400 MHz,CDCl$_3$, TMS): 4.105 (m, 4H), 3.19 (t, 1H), 1.798 (q, 1H), 1.483 (p, 1H), 1.183 (t, 6H), 1.144–1.086 (m, t, 2H), 0.798 (d, 6H)
$^{13}$C-NMR(100 MHz,CDCl$_3$): 169.40, 61.05, 52.09, 36.22, 27.69, 26.56, 22.21, 13.91 ppm (2) Synthesis of ethyl 2-isopropyl-2-isopentylmalonate Into a 2-l flask equipped with an agitator, a Dimroth condenser and a dropping funnel were charged 500 ml of dried ethanol and 250 ml of sodium ethoxide (Aldrich) in a stream of nitrogen. To the mixture was then added 69 g (0.3 mol) of ethyl 2-isopentylmalonate. The reaction mixture was then stirred at room temperature for 30 minutes. To the reaction mixture were then added 73 g (0.6 mol) of isopentyl bromide and 50 ml of ethanol. The reaction mixture was then heated under reflux condition for 24 hours while the reaction was being followed by gas chromatography. To the reaction mixture were then added 300 ml of sodium ethoxide (Aldrich) and 80 g (0.7 mol) of isopentyl bromide. The reaction mixture was then heated under reflux condition for 48 hours. After the completion of the reaction, the reaction mixture was then poured into 500 ml of dilute hydrochloric acid. The reaction mixture was extracted with 200 ml of pentane three times, and then dried over sodium sulfate. The solvent was then distilled off by means of a rotary evaporator. The residue was then distilled under reduced pressure to obtain the desired compound.

Boiling point: 141–150° C./7 mmHg
Yield: 9.3 g (32%)
GC>98.3%
$^1$H-NMR (400 MHz,CDCl$_3$, TMS): 1.844–1.802 (m, 2H), 1.438 (p, 1H), 1.999 (t, 6H), 1.049–0.990 (m, 2H), 0.926 (d, 6H), 0.797 (d, 6H)
$^{13}$C-NMR(100 MHZ,CDCl$_3$): 171.19, 61.489, 60.466, 33.262, 31.490, 31.362, 28.366, 22.272, 18.482, 14.079 ppm (3) Synthesis of ethyl 2-formyl-2-isopropyl-5-methyl-hexanoate Into a 300-ml three-necked flask equipped with a magnetic stirrer and a dropping funnel were charged 100 ml of dried toluene and 6.1 g (0.0224 mol) of ethyl 2-isopropyl-2-isopropentylmalonate in a stream of nitrogen.

The content of the flask was then cooled to a temperature of –78° C. 30 ml (1.5 M/l in toluene) of diisobutylaluminum hydride was then added dropwise to the reaction system with stirring over 30 minutes. At the same temperature, the reaction mixture was then stirred for 1 hour.

50 ml of methyl alcohol was then added to the reaction mixture so that the unreacted diisobutyl aluminum hydride was quenched.

The reaction mixture was then poured into 100 ml of dilute hydrochloric acid. The reaction mixture was extracted with 50 ml of pentane three times, and then dried over sodium sulfate. The solvent was then distilled off by means of a rotary evaporator. The residue was then distilled under reduced pressure to obtain the desired compound.

Boiling point: 129–135° C./22 mmHg
Yield: 5.91 g (nearly 100%)
GC>99%
$^1$H-NMR (400 MHz,CDCl$_3$, TMS): 10.016 (s, 1H), 4.331 (q, 2H), 2.323 (m, 1H), 1.971–1.699 (m, 1H), 1.676–1.580 (m, 1H), 1.563–1.514 (m, 1H), 1.355 (t, 3H), 1.62 (d, 2H), 0.0084–0.915 (m, 12H)
$^{13}$C-NMR(100 MHz,CDCl$_3$): 202.094, 172.405, 63.718, 60.786, (33.518, 33.244), 28.493, 28.293, (22.355, 22.172), 18.427, 17.495, 14.170 ppm (4) Synthesis of ethyl 3-hydroxy-2-isopropyl-2-isopentylpropionate Into a 300-ml three-necked flask equipped with a magnetic stirrer and a dropping funnel were charged 100 ml of dried ethanol and 0.85 g (0.0224 mol) of sodium boron hydride in a stream of nitrogen.

To the reaction mixture was then added dropwise 6.1 g (0.0224 mol) of ethyl 2-formyl-2-isopropyl-5-methyl-hexanoate with stirring at room temperature over 30 minutes. Thereafter, the content of the flask was then heated under reflux condition while the reaction was being followed by gas chromatography.

After the completion of the reaction, the content of the flask was then poured into 100 ml of dilute hydrochloric acid. The reaction mixture was extracted with 50 ml of pentane three times, and then dried over sodium sulfate. The solvent was then distilled off by means of a rotary evaporator. The residue was then distilled under reduced pressure to obtain the desired compound.

Boiling point: 125–133° C./7 mmHg
m/z: 231
Yield: 6.5 g (59%)
GC>98%
$^1$H-NMR (400 MHz,CDCl$_3$, TMS): 4.125 (d, 2H), 3.660 (q, 2H), 2.505 (s, 1H), 1.981 (p, 1H), 1.620–1.555 (m, 1H), 1.499–1.377 (m, 2H), 1.227 (t, 3H), 1.160–1.114 (m, 1H), 0.985–0.970 (m, 1H), 0.885 (d-d, 6H), 0.826 (d, 6H)
$^{13}$C-NMR(100 MHz,CDCl$_3$): 176.94, 63.81, 60.19, 53.27, 33.50, 32.09, 30.0, 28.69, (22.48, 22.37), (18.57, 17.31), 14.17 ppm (5) Synthesis of ethyl 3-methoxy-2-isopropyl-2-isopentylpropionate Into a 500-ml three-necked flask equipped with a magnetic stirrer and a dropping funnel were charged 200 ml of dioxane, 2.75 g (0.0224 mol) of tertiary butoxy potassium and 5.91 g (0.0224 mol) of ethyl 3-hydroxy-2-isopropyl-2-isopentylpropionate. To the reaction mixture was then added dropwise methyl iodide at room temperature over 30 minutes. Thereafter, the content of the flask was heated under reflux condition while the reaction was being followed by gas chromatography.

After the completion of the reaction, the content of the flask was poured into 100 ml of dilute hydrochloric acid. The reaction mixture was extracted with 50 ml of pentane three times, and then dried over sodium sulfate. The solvent was then distilled off by means of a rotary evaporator. The residue was then distilled under reduced pressure to obtain the desired compound.

Boiling point: 126.5–127° C./13 mmHg m/z: 244

Yield: 1.3 g (59%)

GC>99%

$^1$H-NMR (400 MHz, $CDCl_3$, TMS)

4.096 (q, 2H), 3.472 (s, 2H), 3.273 (s, 3H), 1.948 (h, 1H), 1.663–1.570 (m, 2H), 1.446 (h, 1H), 1.214 (t, 3H), 1.149–1.087 (m, 1H), 0.962–0.927 (m, 1H), 0.898 (m, 6H), 0.842 (d, 6H)

Figure 2:
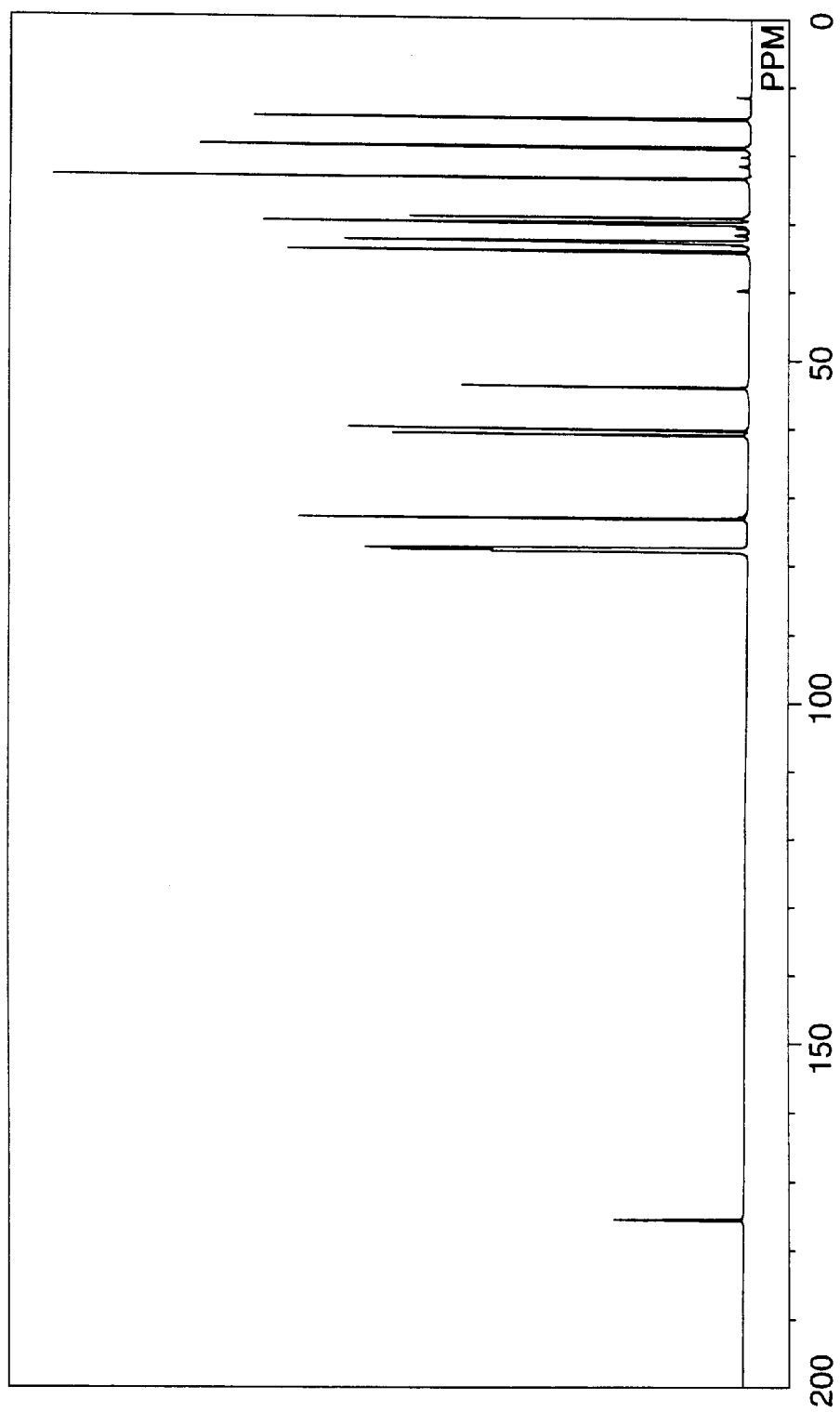
FIG. 2 is $^{13}$C-NMR chart of ethyl 3-methoxy-2-isopropyl-2-isopentylpropionate produced in Example 1.
Figure 3:
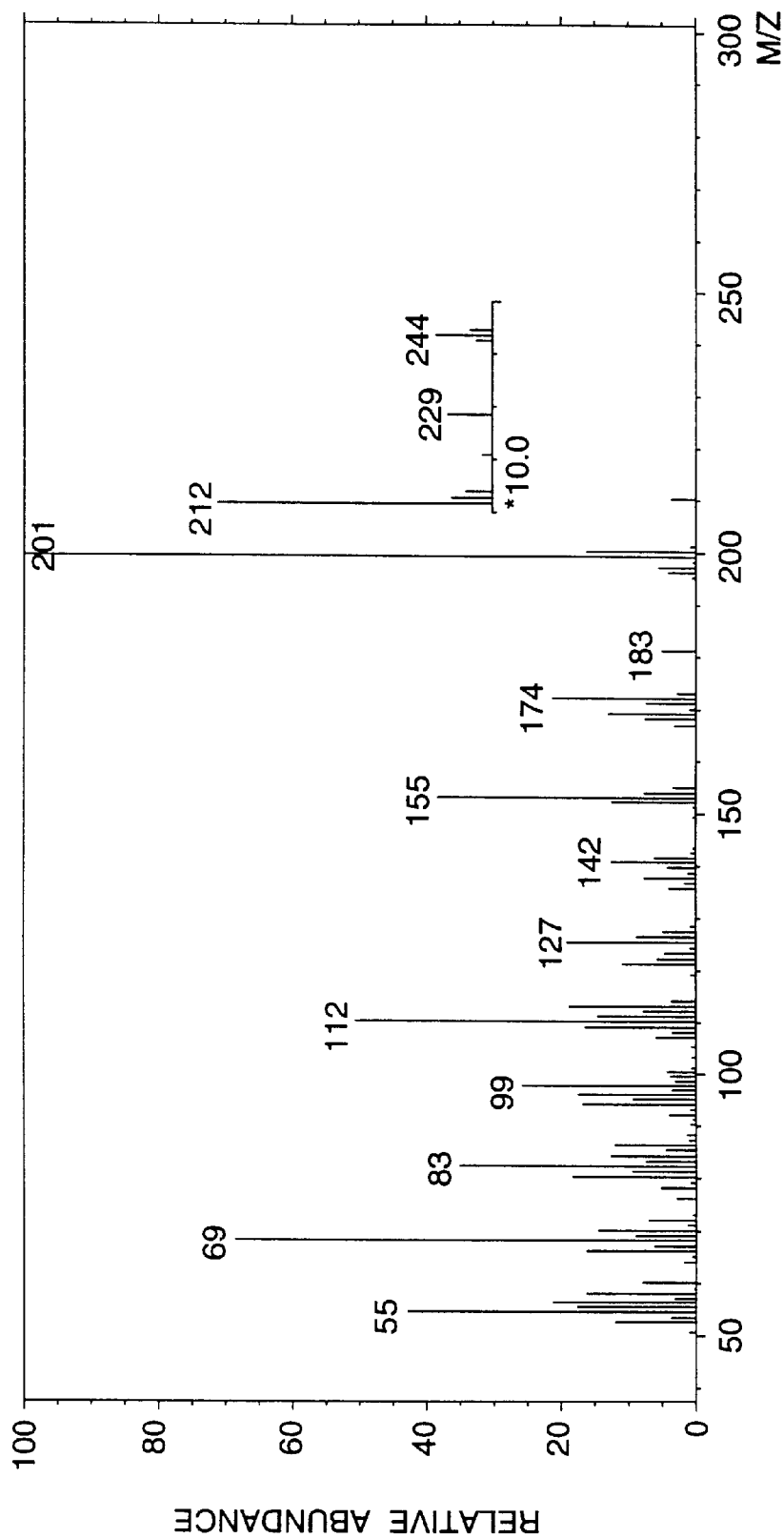
FIG. 3 is GC-MS chart of ethyl 3-methoxy-2-isopropyl-2-isopentylpropionate produced in Example 1.

$^{13}$C-NMR(100 MHz,$CDCl_3$) 174.91, 72.34, 59.88, 52.96, 33.59, 32.22, 29.44, 28.62, 22.57, (18.24, 18.08), 14.28 ppm $^1$H-NMR chart, $^{13}$C-NMR chart and GC-MS chart of the desired compound, ethyl 3-methoxy-2-isopropyl-2-isopentylpropionate, thus obtained are set forth in FIGS. 1 to 3, respectively.

COMPARATIVE EXAMPLE 1

Into a 500-ml three-necked flask equipped with a magnetic stirrer, a dropping funnel and a Dimroth condenser were charged 21 g (0.21 mol) of diisopropylamine and 60 ml of dehydrated tetrahydrofuran in a stream of nitrogen. The content of the flask was then cooled with ice. To the mixture was then added dropwise 132 ml (0.21 mol) of n-butyl lithium (1.7 mol/l hexane solution) over 15 minutes. After the completion of the dropwise addition, the reaction solution was heated to a temperature of 30° C. where it was stirred for 30 minutes. Thereafter, the content of the flask was cooled to a temperature of −78° C. To the reaction mixture were then added dropwise 20 g (0.20 mol) of ethyl 2-isopropyl-2-isopentyl acetate which had been separately synthesized and 30 ml of dehydrated tetrahydrofuran over 30 minutes. The reaction mixture was then stirred for 30 minutes. To the reaction mixture were then added dropwise 21 g (0.265 mol) of chloromethyl methyl ether and 30 mg of dehydrated tetrahydrofuran over 15 minutes. The content of the flask was then sampled and analyzed by gas chromatography. However, the desired compound could not be obtained.

In Example 2 and Comparative Example 2 below, melt flow rate (abbreviated as MFR) was measured in accordance with JIS K-7210-1976 (Table 1; testing condition 14 (testing temperature: 230° C.; test load: 2.16 kg).

Heptane index (abbreviated as H.R.) was the number of the percent residue left after the extraction of the polymer obtained with boiling n-heptane for 6 hours.

In Example 2 and Comparative Example 2, all the starting materials (organic solvent, olefin, hydrogen, titanium compound, magnesium compound, etc.) used in the preparation and polymerization of solid catalyst components had been substantially dehydrated.

The preparation and polymerization of solid catalyst components were effected substantially free from water content in an atmosphere of inert gas such as nitrogen.

EXAMPLE 2

Preparation of solid catalyst component

Into a stainless steel cylindrical vibrating ball milling vessel (filled with ceramic balls having a circular volume of 1 l and a diameter of 10 mm in a proportion of about 50% as calculated in terms of apparent volume) were charged 20 g (0.21 mol) of magnesium chloride anhydride (obtained by drying commercial magnesium chloride anhydride, and then calcining and drying the material in a stream of hydrogen chloride gas at a temperature of about 500° C. for 15 hours), 12.2 g (0.05 mol) of ethyl 3-methoxy-2-propyl-2-isopentylpropionate, 1.5 g of titanium trichloride and 3.0 mol of a silicone oil (TSS-451 available from Shin-Etsu Chemical Co., Ltd.; 20 cs) as a grinding aid in a stream of dried nitrogen. The vessel was then mounted on a vibrating mill having an amplitude of 6 mm. The content of the vessel was then subjected to grinding for 15 hours to obtain a ground solid matter. 15 g of the solid matter was suspended in 150 ml of 1,2-dichloroethane. The suspension was then stirred at a temperature of 80° C. for 2 hours. The solid content was withdrawn by filtration, and then thoroughly washed with hexane until no free 1,2-dichloroethane was detected in wash liquid. The solid content was then dried at a temperature of from 30° C. to 40° C. under reduced pressure so that hexane was removed to obtain a solid catalyst component. The solid catalyst component thus obtained was then analyzed. The content of titanium atom in the solid catalyst component was 2.4% by weight.

(Polymerization and physical properties of polymer produced)

Into a stainless steel autoclave having an inner volume of 3 l were charged 17 mg of the solid catalyst component thus prepared and diethyl aluminum chloride. Into the autoclave were then charged 760 g of propylene and 0.1 g of hydrogen. The autoclave was then heated so that the internal temperature thereof was kept to 70° C. After 1 hour, unreacted gas was released to complete the polymerization. The results of the polymerization are set forth in Table 1.

COMPARATIVE EXAMPLE 2

A solid catalyst component was prepared in the same manner as in Example 1 except that the electron donor was replaced by 13.9 g (0.05 mol) of dibutyl phthalate. The solid catalyst component thus prepared was then evaluated for polymerizability in the same manner as in Example 1. The results are set forth in Table 1.

TABLE 1

| | Amount of catalyst (mg) | Amount of Al (mg) | Yield (g) | H.R. (%) | MFR (g/10 min) |
| --- | --- | --- | --- | --- | --- |
| Example 2 | 34.0 | 96.0 | 126 | 94.1 | 4.5 |
| Comparative Example 2 | 44.0 | 96.0 | 68 | 54.8 | 66.0 |

In Examples 3 to 21 and Comparative Examples 3 to 12 below, the percent xylene soluble content of polymer at room temperature (XSRT %) was defined as the residue obtained by dissolving 2 g of a polymer in 200 ml of xylene at a temperature of 135° C., cooling the solution to room temperature to precipitate the polymer, filtrating the polymer thus precipitated under reduced pressure, subjecting the filtrate to distillation by a rotary evaporator to remove the solvent, and then drying the residue.

XSRT (%) was calculated by the following equation:

$$XSRT\ (\%) = \frac{\text{Number of grams of residue}}{\text{Number of grams of sample polymer}} \times 100$$

The polymerization activity was calculated by the following equation:

$$\text{Polymerization activity } (R.R.)(g/gh) =$$

$$\frac{\text{Number of grams of polymer obtained}}{(\text{Number of grams of solid catalyst}) \times (\text{polymerization time})}$$

The melt flow rate (MFR) at a load of 2.16 kg as used in Examples 3 to 21 and Comparative Examples 3 to 12 was measured in accordance with JIS K-6758-1968.

The initial flexural modulus of elasticity (FM) as used in Examples 3 to 21 and Comparative Examples 3 to 12 was measured in accordance with ASTM-D-790-6600.

The content of silicon atom in the polymer was measured by means of a fluorescent X-ray analyzer.

The percent heptane index (abbreviated as H.R.) as a measure of the stereoregularity of the polymer was the percent residue left after the extraction of the polymer obtained with boiling n-heptane for 6 hours.

In Examples 3 to 21 and Comparative Examples 3 to 12, all the compounds used in the preparation and polymerization of solid catalyst components (organic solvent, olefin, hydrogen, titanium compound, magnesium compound, etc.) had been substantially dehydrated.

The preparation and polymerization of the solid catalyst components were effected substantially free from water content in an atmosphere of an inert gas such as nitrogen.

The organoaluminum compound and electron donors used in the polymerization process were used in the form of 1.0 M/l hexane solution and 0.1 M/l hexane solution, respectively.

The organoaluminum compounds and electron donors (E.D.) used in Examples 3 to 16 and Comparative Examples 3 to 10 are abbreviated or symbolized as follows: Triethyl aluminum (TEA), triisobutyl aluminum (TIBA), ethyl 2-isopropyl-2-isopentyl-3-methoxy-propionate (A), methyl 2-isopropyl-2-isopentyl-3-methoxy-propionate (B), ethyl 2-cyclopentyl-2-isopentyl-3-methoxy-propionate (C), ethyl 2,2-dicyclopentyl-3-methoxy-propionate (D), diisobutyl phthalate (E), ethyl 2-tert-butyl-3-methoxy-propionate (F), 2,2-diisobutyl-1,3-dimethoxypropane (G)

EXAMPLE 3

Preparation of solid catalyst component

Into a stainless steel cylindrical vibrating ball milling vessel (filled with ceramic balls having a circular volume of 1 l and a diameter of 10 mm in a proportion of about 50% as calculated in terms of apparent volume) were charged 20 g (0.21 mol) of magnesium chloride anhydride (obtained by drying commercial magnesium chloride anhydride, and then calcining and drying the material in a stream of hydrogen chloride gas at a temperature of about 500° C. for 15 hours), 12.2 g (0.05 mol) of ethyl 2-isopropyl-2-isopentyl-3- methoxy-propionate, 3.0 ml of titanium tetrachloride and 3.0 mol of a silicone oil (TSS-451 available from Shin-Etsu Chemical Co., Ltd.; 20 cs) as a grinding aid in a stream of dried nitrogen. The vessel was then mounted on a vibrating mill having an amplitude of 6 mm. The content of the vessel was then subjected to grinding for 15 hours to obtain a ground solid matter. 15 g of the solid matter was suspended in 150 ml of 1,2-dichloroethane. The suspension was then stirred at a temperature of 80° C. for 2 hours. The solid content was withdrawn by filtration, and then thoroughly washed with hexane until no free 1,2-dichloroethane was detected in wash liquid. The solid content was then dried at a temperature of from 30° C. to 40° C. under reduced pressure so that hexane was removed to obtain a solid catalyst component. The solid catalyst component thus obtained was then analyzed. The content of titanium atom in the solid catalyst component was 2.4% by weight.

Polymerization and physical properties of polymer produced

Into a stainless steel autoclave having an inner volume of 3 l were charged 17 mg of the solid catalyst component thus prepared and 91 mg of triethyl aluminum. Into the autoclave were then charged 760 g of propylene and 0.1 g of hydrogen. The autoclave was then heated so that the internal temperature thereof was kept to 70° C. After 1 hour, the gas content was released to complete the polymerization. The results of the polymerization are set forth in Table 1.

EXAMPLE 4 AND COMPARATIVE EXAMPLES 3 AND 4

Solid catalyst components were prepared in the same manner as in Example 3 except that the electron donor was replaced by the compounds set forth in Table 2. These solid catalyst components were then evaluated for polymerization properties. The results are set forth in Table 2.

EXAMPLE 5

Preparation of solid catalyst component 9.5 g of magnesium chloride anhydride (treated in the same manner as in Example 3) was heated and dissolved in a mixture of 50 ml of decane and 48.6 ml of 2-ethylhexyl alcohol at a temperature of 130° C. in an atmosphere of nitrogen in a round flask for 2 hours. To the solution was then added 2.1 g of phthalic anhydride. The solution was further heated to a temperature of 130° C. for 1 hour. The solution was then allowed to cool to room temperature. 20 ml of the solution was then charged into a dropping funnel. The solution was then added dropwise to 80 ml of titanium tetrachloride at −20° C. over 30 minutes. The mixture was then heated to a temperature of 110° C. in 4 hours. A solution of 1.22 g (0.005 mol) of ethyl 2-isopropyl-2-isopentyl-3-methoxy-propionate in 5 ml of hexane was then gradually added dropwise to the mixture. After the completion of the dropwise addition, the mixture was allowed to undergo reaction at a temperature of 110° C. for 2 hours. The resulting supernatant liquid was then removed. 80 ml of titanium tetrachloride was then introduced into the reaction system. The reaction system was then heated to a temperature of 110° C. for 2 hours. The reaction product was washed with 100 ml of decane three times and then with hexane to obtain a solid catalyst. The supported amount of titanium was 2.6% by weight.

Polymerization and physical properties of polymer produced

Into a stainless steel autoclave having an inner volume of 3 l were charged 8.8 mg of the solid catalyst component thus prepared and 182 mg of triethyl aluminum. Into the autoclave were then charged 760 g of propylene and 0.1 g of hydrogen. The autoclave was then heated so that the internal temperature thereof was kept to 80° C. After 1 hour, the gas content was released to complete the polymerization. The results of the polymerization are set forth in Table 2.

EXAMPLES 6 AND 7 AND COMPARATIVE EXAMPLES 5 AND 6

Solid catalyst components were prepared in the same manner as in Example 5 except that the electron donor was replaced by the compounds set forth in Table 2. These solid catalyst components were evaluated for polymerization properties. The results are set forth in Table 2.

EXAMPLE 8

Preparation of solid catalyst component

Into a 300-ml round flask which had been thoroughly dried were charged 5.0 g of diethoxy magnesium, 1.22 g (0.005 mol) of ethyl 2-isopropyl-2-isopentyl-3-methoxy-propionate and 25 ml of methylene chloride in a stream of nitrogen. The reaction mixture was then stirred under reflux for 1 hour. The resulting suspension was then pressed into 200 ml of titanium tetrachloride at room temperature. The reaction mixture was then gradually heated to a temperature of 110° C. where it was allowed to undergo reaction with stirring for 2 hours. After the completion of the reaction, a solid matter was precipitated. The solid matter thus precipitated was then withdrawn by filtration. The solid matter was washed with 200 ml of decane of 110° C. three times, and then washed with hexane at room temperature until no chlorine ions were detected. The content of titanium atom in the catalyst component was 3.3% by weight.

Polymerization and physical properties of polymer produced

Into a stainless steel autoclave having an inner volume of 3 l were charged 2.5 mg of the solid catalyst component thus prepared and 182 mg of triethyl aluminum. Into the autoclave were then charged 760 g of propylene and 0.1 g of hydrogen. The autoclave was then heated so that the internal temperature thereof was kept to 80° C. After 1 hour, the gas content was released to complete the polymerization. The results of the polymerization are set forth in Table 1.

EXAMPLES 9 AND 10 AND COMPARATIVE EXAMPLES 7 AND 8

Solid catalyst components were prepared in the same manner as in Example 8 except that the electron donor was replaced by the compounds set forth in Table 2. These solid catalyst components were evaluated for polymerization properties. The results are set forth in Table 2.

EXAMPLE 11

Preparation of solid catalyst component 12.8 g of metallic magnesium, 88 ml (0.53 mol) of ethyl orthoformate and 0.5 ml of 1,2-dibromoethane as a reaction initiator were mixed. The suspension thus obtained was then kept at a temperature of 55° C. To the suspension was then added 5 ml out of a solution of 80 ml (0.80 mol) of n-butyl chloride in 100 ml of hexane. The mixture was then stirred for 50 minutes. The rest of the solution was then added dropwise to the mixture over 80 minutes. The reaction mixture was then allowed to undergo reaction at a temperature of 70° C. with stirring for 4 hours to obtain a solid product. The solid product was then washed with hexane six times at a temperature of 50° C.

6.3 g of the solid product thus obtained and 50 ml of decane were then charged into the reaction vessel. To the mixture was then added dropwise a mixture of 2.0 ml of 2,2,2-trichloroethanol and 11 ml of decane at room temperature over 30 minutes. After the completion of the dropwise addition, the reaction mixture was stirred at a temperature of 80° C. for 1 hour. The resulting solid matter was withdrawn by filtration, washed with 100 ml of hexane four times, and then washed with 100 ml of toluene twice.

To 40 ml of the solid matter thus obtained was then added 60 ml of titanium tetrachloride. The mixture was then heated to a temperature of 90° C. To the mixture was then added dropwise a solution of 1.83 g (0.0075 mol) of ethyl 2-isopropyl-2-isopentyl-3-methoxy-propionate in 5 ml of toluene over 5 minutes. The mixture was then stirred at a temperature of 120° C. for 2 hours. Thereafter, the resulting solid matter was withdrawn by filtration at a temperature of 90° C., and then washed with toluene twice at the same temperature. To the solid matter were then added 40 ml of toluene and 60 ml of titanium tetrachloride. The mixture was then stirred at a temperature of 120° C. for 2 hours. The resulting solid matter was withdrawn by filtration at a temperature of 110° C., and then washed with 100 ml of hexane seven times at room temperature to obtain a solid titanium catalyst component.

Polymerization and physical properties of polymer produced

Into a stainless steel autoclave having an inner volume of 3 l were charged 4.6 mg of the solid catalyst component thus prepared and 182 mg of triethyl aluminum. Into the autoclave were then charged 760 g of propylene and 0.1 g of hydrogen. The autoclave was then heated so that the internal temperature thereof was kept to 80° C. After 1 hour, the gas content was released to complete the polymerization. The results of the polymerization are set forth in Table 2.

EXAMPLES 12 TO 16 AND COMPARATIVE EXAMPLES 9 AND 10

Solid catalyst components were prepared in the same manner as in Example 11 except that the electron donors and the organoaluminum compound were replaced by the compounds set forth in Table 2. These solid catalyst components were then evaluated for polymerization properties. The results are set forth in Table 2.

TABLE 2

|  | E.D. | Al compound | Amount of catalyst (mg) | Amount of Al compound (mg) | R.R. (g/gh) | H.R. (%) | MFR (g/10 min) |
| --- | --- | --- | --- | --- | --- | --- | --- |
| Example 3 | A | TEA | 17.0 | 91.0 | 12,700 | 92.3 | 7.4 |
| Example 4 | C | TEA | 19.0 | 91.0 | 11,800 | 89.0 | 11.6 |
| Comparative Example 3 | E | TEA | 22.0 | 91.0 | 10,100 | 46.7 | 56.0 |

TABLE 2-continued

|  | E.D. | Al compound | Amount of catalyst (mg) | Amount of Al compound (mg) | R.R. (g/gh) | H.R. (%) | MFR (g/10 min) |
|---|---|---|---|---|---|---|---|
| Comparative Example 4 | G | TEA | 19.0 | 91.0 | 8,300 | 82.0 | 21.0 |
| Example 5 | A | TEA | 8.8 | 182.0 | 20,500 | 98.5 | 3.4 |
| Example 6 | B | TEA | 6.7 | 182.0 | 17,500 | 97.4 | 3.9 |
| Example 7 | D | TEA | 7.2 | 182.0 | 22,300 | 98.1 | 3.9 |
| Comparative Example 5 | E | TEA | 4.9 | 182.0 | 17,000 | 52.2 | 46.0 |
| Comparative Example 6 | F | TEA | 5.6 | 182.0 | 16,200 | 93.4 | 17.2 |
| Example 8 | A | TEA | 2.5 | 182.0 | 34,000 | 98.7 | 2.4 |
| Example 9 | B | TEA | 3.0 | 182.0 | 27,700 | 96.3 | 5.8 |
| Example 10 | C | TEA | 3.2 | 182.0 | 32,100 | 98.1 | 2.9 |
| Comparative Example 7 | E | TEA | 5.1 | 182.0 | 25,200 | 56.4 | 68.0 |
| Comparative Example 8 | F | TEA | 4.2 | 182.0 | 27,600 | 94.2 | 11.3 |
| Example 11 | A | TEA | 4.6 | 182.0 | 36,000 | 98.2 | 3.7 |
| Example 12 | B | TEA | 5.3 | 182.0 | 28,800 | 96.6 | 6.0 |
| Example 13 | D | TEA | 4.7 | 182.0 | 32,800 | 97.5 | 5.5 |
| Example 14 | A | TIBA | 4.4 | 420.0 | 43,200 | 97.3 | 8.2 |
| Example 15 | B | TIBA | 4.7 | 420.0 | 37,700 | 95.4 | 4.6 |
| Example 16 | D | TIBA | 5.1 | 420.0 | 41,300 | 95.7 | 4.7 |
| Comparative Example 9 | E | TEA | 6.1 | 182.0 | 23,600 | 62.2 | 47.0 |
| Comparative Example 10 | F | TEA | 4.6 | 182.0 | 24,600 | 94.6 | 16.0 |

EXAMPLE 17

Preparation of solid titanium catalyst component (A)

1.71 g of magnesium chloride anhydride, 9 ml of decane and 8.4 ml of 2-ethylhexyl alcohol were heated to a temperature of 130° C. for 3 hours to undergo reaction to make a homogeneous solution. To the solution thus obtained was then added 0.39 g of phthalic anhydride. The reaction mixture was then stirred at a temperature of 130° C. for 2 hours so that phthalic anhydride was dissolved in the homogeneous solution. The homogeneous solution thus obtained was then allowed to cool to room temperature. The solution was then added dropwise to 72 ml of titanium tetrachloride which had been kept to a temperature of −20° C. over 1 hour. After the completion of the dropwise addition, the mixture was heated to a temperature of 110° C. over 4 hours. When the temperature of the mixture reached 110° C., 0.91 g of diisobutyl phthalate was added to the mixture. The mixture was then stirred and kept at the same temperature for 2 hours. After the completion of the reaction, a solid matter was withdrawn by hot filtration. The solid matter was then re-suspended in 72 ml of titanium tetrachloride. The suspension was then subjected to heat reaction at a temperature of 110° C. for 2 hours. After the completion of the reaction, a solid matter was withdrawn by hot filtration. The solid matter was thoroughly washed with decane and hexane until no chlorine ion was detected in the wash liquid, and then dried under reduced pressure.

Polymerization

Into a 6.0-l stainless steel autoclave were charged 4.8 mg of the solid component thus prepared, 1.6 ml of ethyl 2-isopropyl-2-isopentyl-3-methoxy-propionate (0.1 M/l hexane solution) and 1.6 ml of triethyl aluminum (1.0 M/l hexane solution). To the reaction mixture were then added 1,020 g of propylene and 0.09 g of hydrogen. The autoclave was then heated so that the inner temperature thereof was kept at 70° C. After 2 hours, the gas content was released to complete the polymerization. The results are set forth in Table 3.

COMPARATIVE EXAMPLE 11

A catalyst was prepared and polymerization was effected in the same manner as in Example 17 except that the catalyst component (C) used was replaced by the compound set forth in Table 3. The results of the polymerization are set forth in Table 3.

EXAMPLE 18

Preparation of solid titanium catalyst component (A)

Into a 300-ml round flask which had been thoroughly dried were charged 5 g of diethoxy magnesium, 1.30 g of ethyl 3-methoxy-2-tert-amyl-propionate and 25 ml of methylene chloride in a stream of nitrogen. The mixture was then stirred under reflux for 1 hour. The resulting suspension was then pressed into 200 ml of titanium tetrachloride at room temperature. The mixture was gradually heated to a temperature of 110° C. where it was allowed to undergo reaction with stirring for 2 hours. After the completion of the reaction, the solid matter thus precipitated was withdrawn by filtration, and then washed with 200 ml of n-decane of 110° C. three times. To the product was then added 200 ml of titanium tetrachloride. The reaction mixture was then allowed to undergo reaction at a temperature of 120° C. for 2 hours. After the completion of the reaction, the solid matter thus precipitated was washed with 200 ml of n-decane three times, and then washed with n-hexane until no chlorine ions were detected.

Polymerization

Into a 6.0-l stainless steel autoclave were charged 5.2 mg of the solid component thus prepared, 1.6 ml of ethyl 2-isopropyl-2-isopentyl-3-methoxy-propionate (0.1 M/l hexane solution) and 1.6 ml of triethyl aluminum (1.0 M/l hexane solution). To the mixture were then added 340 g of propylene and 0.09 g of hydrogen. The autoclave was then heated so that the inner temperature thereof was kept at 80° C. After 2 hours, the content gas was released to complete polymerization. The results are set forth in Table 3.

COMPARATIVE EXAMPLE 12 AND EXAMPLES 19 TO 21

A catalyst was prepared and polymerization was effected in the same manner as in Example 18 except that the catalyst component (C) used was replaced by the compounds set forth in Table 3. The results of the polymerization are set forth in Table 3.

TABLE 3

| | Component (C) | Catalyst activity (g/gh) | XSRT (%) | MFR (g/10 min) | FM (Kg/cm²) | Si content (ppm) |
|---|---|---|---|---|---|---|
| Example 17 | a | 22,600 | 3.2 | 5.7 | 16,600 | <1 |
| Comparative Example 11 | e | 23,000 | 2.8 | 5.3 | 15,300 | 12 |
| Example 18 | a | 29,400 | 3.4 | 6.4 | 16,200 | <1 |
| Example 19 | b | 33,400 | 2 | 7.3 | 16,500 | <1 |
| Example 20 | c | 26,000 | 2.3 | 7.7 | 17,100 | <1 |
| Example 21 | d | 32,300 | 2.1 | 5 | 17,000 | <1 |
| Comparative Example 12 | e | 21,300 | 3 | 6.1 | 15,500 | 8 |

Component (C) in Table 3
a: Ethyl 2-isopropyl-2-isopentyl-3-methoxypropionate
b: Ethyl 2-isopropyl-2-cyclopentyl-3-methoxypropionate
c: Ethyl 2,2-diisobutyl-3-methoxypropionate
d: Ethyl 2,2-dicyclopentyl-3-methoxypropionate
e: Cyclohexylmethyl dimethoxysilane In accordance with the present invention, the following effects can be exerted.

A novel ester compound containing an ester group and an alkoxy group in its molecule and two alkyl substituents, particularly bulky substituents at the α-position with respect to the ester group which can be used as an electron donor for Ziegler-Natta catalyst can be provided.

In accordance with the process of the present invention, an olefin polymer which is free of any silanol compound or siloxane having a great effect on the physical properties thereof and thus exhibits practically excellent properties can be produced.

Further, an olefin polymerization solid catalyst component which exhibits a high activity and a high stereoregularity, an olefin polymerization catalyst and a process for the preparation of an olefin polymer in the presence of such an olefin polymerization catalyst can be provided without using any expensive organosilicon compound and causing any safety and hygienic problems.

While the invention has been described in detail and with reference to specific embodiments thereof, it will be apparent to one skilled in the art that various changes and modifications can be made therein without departing from the spirit and scope thereof.

What is claimed is:

1. A 3-alkoxypropionic ester derivative, represented by formula (I):

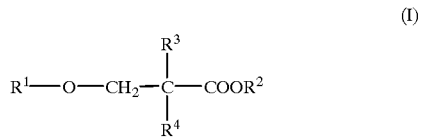

wherein $R^1$ represents a hydrocarbon group having from 1 to 10 carbon atoms; $R^2$ represents a hydrocarbon group having from 1 to 20 carbon atoms; $R^3$ represents a hydrocarbon group having from 1 to 20 carbon atoms; and $R^4$ is selected from the group consisting of isopropyl, isobutyl, isopentyl and cyclopentyl.

2. A 3-alkoxypropionic ester derivative as claimed in claim 1, wherein $R^1$ represents a methyl group, an ethyl group, or a propyl group; $R^2$ represents a hydrocarbon group having from 1 to 10 carbon atoms; $R^3$ represents a methyl group, an ethyl group, an iospropyl group, a butyl group, an isobutyl group, a pentyl group, an isopentyl group, a hexyl group, a heptyl group, an octyl group, a 2-ethylhexyl group, a decyl group, a pentadecyl group, a cyclopentyl group, or a cyclohexyl group; and $R^4$ is selected from the group consisting of isopropyl, isobutyl, isopentyl and cyclopentyl.

3. A 3-alkoxypropionic ester derivative as claimed in claim 1, wherein $R^1$ represents a methyl group; $R^2$ reprents a lower alkyl group having from 1 to 4 carbon atoms; $R^3$ represents an isopropyl group; and $R^4$ represents an isopentyl group.

4. A 3-alkoxypropionic ester derivative as claimed in claim 3, wherein $R^1$ represents a methyl group; $R^2$ represents an ethyl group; $R^3$ represents an isopropyl group; and $R^4$ represents an isopentyl group.

5. A 3-alkoxypropionic ester derivative as claimed in claim 1, which is ethyl 2,2-diisobutyl-3-methoxypropionate, methyl 2-isopropyl-2-isopentyl-3-methoxypropionate, ethyl 2-isopropyl-2-isopentyl-3-methoxypropionate, methyl 2-isopropyl-2-cyclopentyl-3-methoxypropionate, ethyl 2-isopropyl-2-cyclopentyl-3-methoxypropionate, methyl 2-cyclopentyl-2-isopentyl-3-methoxypropionate, ethyl 2-cyclopentyl-2-isopentyl-3-methoxypropionate, methyl 2,2-dicyclopentyl-3-methoxypropionate, or ethyl 2,2-dicyclopentyl-3-methoxypropionate.

* * * * *